United States Patent [19]

Bartmann et al.

[11] 4,260,611
[45] Apr. 7, 1981

[54] ISOQUINOLINE DERIVATIVES

[75] Inventors: Wilhelm Bartmann; Elmar Konz, both of Bad Soden am Taunus, Fed. Rep. of Germany

[73] Assignee: Hoechst Aktiengesellschaft, Frankfurt am Main, Fed. Rep. of Germany

[21] Appl. No.: 76,204

[22] Filed: Sep. 17, 1979

Related U.S. Application Data

[63] Continuation-in-part of Ser. No. 33,326, Apr. 25, 1979, abandoned.

[30] Foreign Application Priority Data

Apr. 27, 1978 [DE] Fed. Rep. of Germany ....... 2818423

[51] Int. Cl.³ .................. A61K 31/47; C07D 217/14; C07D 217/16; C07D 217/24
[52] U.S. Cl. .................................... 424/250; 424/258; 544/363; 546/90; 546/139; 546/145; 546/146; 546/147
[58] Field of Search ............... 544/363; 546/145, 146, 546/147, 139; 424/250, 258

[56] References Cited

U.S. PATENT DOCUMENTS 3,930,837  1/1976  Serban .................................. 546/145

*Primary Examiner*—Paul M. Coughlan, Jr.
*Attorney, Agent, or Firm*—Curtis, Morris & Safford

[57] ABSTRACT

Isoquinoline derivatives of the formula

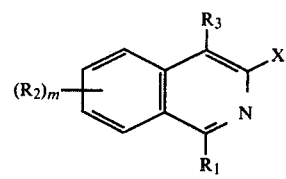

wherein the substituent is such as chlorine or bromine; $R_1$ is phenyl etc.; $R_2$ is hydrogen, halogen etc.; $R_3$ is e.g. aminoalkyl and their use as medicaments, in particular as antidepressants.

5 Claims, No Drawings

ISOQUINOLINE DERIVATIVES

This application is a continuation-in-part application of U.S. patent application Ser. No. 033,326, filed Apr. 25, 1979, now abandoned.

The present invention relates to novel substituted isoquinoline derivatives having valuable pharmacological, in particular antidepressive properties.

Subject of the present invention are, consequently, isoquinoline derivatives of the formula

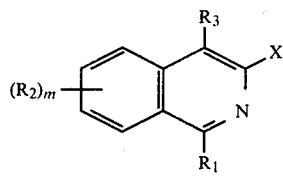

I and their physiologically acceptable salts, wherein
m is 1 or 2,
X is a bromine or chlorine,
$R_1$ is pyridyl, phenyl, thienyl, a phenyl mono- or di-substituted by halogen; hydroxy; nitro; unsubstituted amino or amino substituted by one or two aliphatic, cycloaliphatic or aromatic hydrocarbons radicals of two to eighteen carbon atoms, the nitrogen atom of said amino being optionally included in a heterocyclic ring; acylamino; alkyl or alkoxy each having one to six carbon atoms; benzyloxy or trifluoromethyl;
$R_2$ is hydrogen; halogen; hydroxy; alkyl or alkoxy each having one to six carbon atoms; nitro; amino; benzyloxy; methylenedioxy or ethylenedioxy;
$R_3$ is carboxyl; cyano; hydroxymethyl; alkoxymethyl having from 2 to 7 carbon atoms; aminomethyl of the formula

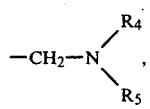

wherein $R_4$ and $R_5$ are identical or different and denote hydrogen or straight chain or branched, saturated or unsaturated alkyl of from 1 to 8 carbon atoms optionally substituted by hydroxy, $C_{1-4}$ alkoxy or amino of the formula

wherein $R_6$ and $R_7$ are identical or different and denote straight chain or branched alkyl having from 1 to 6 carbon atoms or, when taken together, a heterocyclic ring having up to 7 carbon atoms; $R_4$ and $R_5$ may furthermore form a five- to eight-membered heterocyclic ring with the nitrogen atom, the heterocyclic ring being optionally substituted at one carbon atom by $C_1$-$C_6$ alkyl, $C_1$-$C_4$ alkoxy, hydroxy, carboxy or $C_1$-$C_4$ alkoxycarbonyl and one of the carbon atoms of the heterocyclic ring being optionally replaced by an oxygen, sulfur or nitrogen, the latter being optionally substituted by hydrogen, thienyl, furyl, pyridyl or formyl, $C_3$-$C_8$ alkenyloxycarbonyl or $C_3$-$C_8$ alkinyloxycarbonyl, $C_2$-$C_7$ alkoxycarbonyl optionally substituted by hydroxy or $C_1$-$C_4$ alkoxy, phenyl optionally substituted once or several times by $C_1$-$C_4$ alkyl, $C_1$-$C_4$ alkoxy, methylenedioxy, hydroxy, nitro, amino or halogen and the hydrogen atom at the nitrogen atom being further substituted optionally by —$COR_8$ wherein $R_8$ denotes thienyl, furyl, pyridyl or phenyl, optionally substituted as specified above, $C_1$-$C_6$ alkyl, the latter being optionally substituted by hydroxy, $C_1$-$C_4$ alkoxy, $C_1$-$C_6$ dialkylamino, ethylenedioxy, trimethylenedioxy or phenyl optionally substituted as specified above and $R_3$ may further be a carboxylic group of the formula

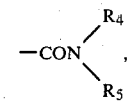

wherein $R_4$ and $R_5$ are defined as above.

The present invention relates in particular to compounds wherein m is 1 or 2; X is chlorine; $R_1$ is phenyl optionally mono- or disubstituted by halogen; hydroxy; nitro; unsubstituted amino or amino substituted by one or two aliphatic, cycloaliphatic or aromatic hydrocarbon atoms and having from two to twelve carbon atoms, the nitrogen atom of amino being optionally included in a heterocyclic ring; acylamino, alkyl or alkoxy each having from one to four carbon atoms; benzyloxy or trifluoromethyl; or $R_1$ is pyridyl; $R_2$ is hydrogen; halogen, hydroxy; nitro; amino; alkyl or alkoxy having from one to four carbon atoms and $R_3$ is carboxyl; cyano; hydroxymethyl; alkoxymethyl having from one to four carbon atoms; aminomethyl of the formula

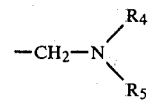

or a carboxylic amide group of the formula

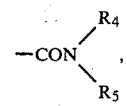

wherein $R_4$ and $R_5$ are identical or different and denote straight chain or branched, saturated or unsaturated alkyl having from one to four carbon atoms and, when taken together, optionally forming a five- to eight-membered ring, one of the carbon atoms of this ring being optionally substituted by oxygen, sulfur or nitrogen, the latter being optionally substituted by hydrogen, thienyl, furyl, pyridyl or formyl, $C_1$-$C_4$ alkoxycarbonyl optionally substituted by hydroxy or $C_1$-$C_4$ alkoxy, phenyl optionally substituted once or several times by $C_1$-$C_4$ alkyl, $C_1$-$C_4$ alkoxy, methylenedioxy, hydroxy, nitro or amino, or halogen and the hydrogen atom at the nitrogen atom being further replaced optionally by —$COR_8$, wherein $R_8$ denotes thienyl, furyl, pyridyl or phenyl, optionally substituted as specified above, or by $C_1$-$C_4$ alkyl optionally substituted by hydroxy, $C_1$-$C_4$ alkoxy, $C_1$-$C_4$ dialkylamino or phenyl optionally substituted as specified above, or, in which formula, when $R_4$ is hydrogen or $C_1$-$C_4$ alkyl, $R_5$ is aminoalkyl of the formula

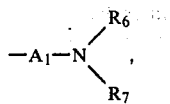

with $A_1$ denoting straight chain or branched $C_2-C_6$ alkylene optionally substituted by hydroxy or $C_1-C_4$ alkoxy and $R_6$ and $R_7$ being specified as above.

Particularly interesting are compounds wherein
m is one or two;
X is chlorine;
$R_1$ is phenyl optionally mono- or disubstituted by halogen, hydroxy, nitro, amino, $C_1-C_4$ alkyl; methoxy or trifluoromethyl;
$R_2$ is hydrogen; halogen; hydroxy; nitro; amino; $C_1-C_4$ alkyl or alkoxy having from 1 to 4 carbon atoms and
$R_3$ is carboxyl; cyano; hydroxymethyl or aminomethyl of the formula

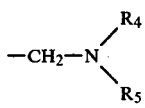

or a carboxylic amide of the formula

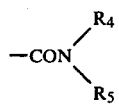

in which the alkyl radicals $R_4$ and $R_5$ form a five- to seven-membered ring, when taken together with the nitrogen atom, one of the carbon atoms whereof may be replaced by nitrogen or oxygen, for example pyrrolidino, piperidino, hexamethylenimino, morpholino, 4-hydroxypiperidino, 4-carboethoxypiperidino and 1-piperazinyl of the formula

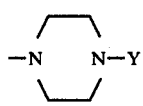

in which Y is hydrogen; $C_1-C_4$ alkyl; β-hydroxyethyl; 3,4-methylene-dioxybenzyl; unsubstituted phenyl or phenyl substituted by methoxy, chloro, nitro or amino; 3,4,5-trimethoxybenzoyl; 3,4-methylene-dioxybenzoyl; 2-furoyl; 2thienoyl; $C_1-C_3$ alkoxycarbonyl, the alkyl radical of the latter being optionally substituted by OH, methoxy or ethoxy, or, in which formula, when $R_4$ is hydrogen or $C_1-C_4$ alkyl, $R_5$ is aminoalkyl of the formula

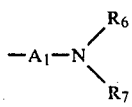

with $A_1$, $R_6$ and $R_7$ being defined as above.

The process for the preparation of the compounds of the formula I comprises (a) oxidizing compounds of the formula II

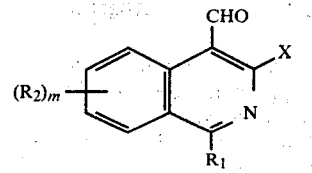

wherein X, $R_1$, $R_2$ and m are defined as in formula I, to give compounds of the formula I wherein $R_3$ is carboxyl. The latter compounds may be reacted with an amine of the formula

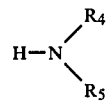

wherein $R_4$ and $R_5$ are defined as in formula I, to give compounds of the formula I wherein $R_3$ is carboxylic amide of the formula

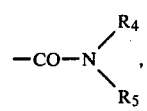

(b) reducing compounds of the formula III

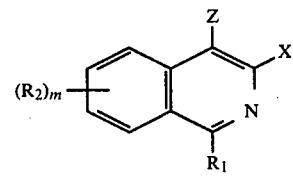

wherein Z is formyl, nitril, carboxy, halogenocarboxyl or alkylcarboxyl having from 1 to 7 carbon atoms and X, $R_1$, $R_2$ and m are defined as in formula I, to give compounds of the formula I wherein $R_3$ is hydroxymethyl, (c) reducing compounds of the formula IV

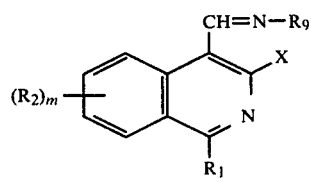

wherein X, $R_1$, $R_2$ and m are defined as in formula I, to give compounds of the formula I wherein $R_3$ is methylenamino of the formula $-CH_2-NH-R_9$ with $R_9$ denoting the radical

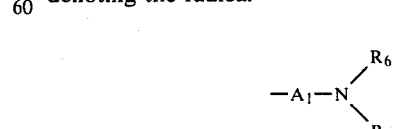

wherein A, $R_6$ and $R_7$ are defined as in formula I, (d) reacting compounds of the formula V

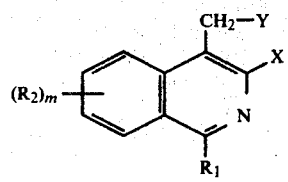

wherein Y is chlorine, bromine or hydroxy and X, $R_1$, $R_2$ and m are defined as in formula I, with an amine of the formula

with $R_4$ and $R_5$ being defined as in formula I, $R_3$ is the group

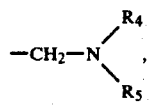

(e) converting compounds of the formula VI

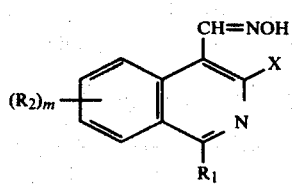

wherein X, $R_1$, $R_2$ and m are defined as in formula I, with agents splitting off water into compounds of the formula I wherein $R_3$ is nitril, (f) reacting compounds of the formula VII

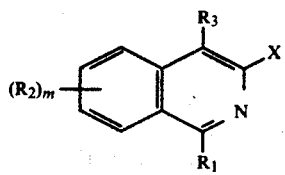

wherein X, $R_1$, $R_2$, $R_3$ and m are defined as in formula I, provided that in one of the radicals or in both of the radicals $R_1$ and $R_3$ a secondary amino group is included, with an alkylation agent of the formula Y—$R_{10}$, wherein Y is iodine, chlorine or bromine, and $R_{10}$ is straight chain or branched $C_1$-$C_6$ alkyl, optionally substituted by hydroxy-$C_1$-$C_4$ alkoxy, $C_1$-$C_4$ dialkylamino, ethylenedioxy, trimethylenedioxy or optionally substituted phenyl, or $R_{10}$ is $C_3$-$C_8$ alkenyl or $C_3$-$C_8$ alkinyl, or reacting compounds of the formula VII with a chloroformate of the formula Cl—$CO_2$($C_1$-$C_4$) alkyl, the alkyl radicals being substituted by hydroxy or $C_1$-$C_4$ alkoxy, or reacting compounds of the formula VII with a compound of the formula Cl—$COR_8$ with $R_8$ being defined as in formula I, (g) in compounds of the formula I

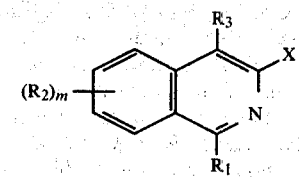

wherein X, $R_1$, $R_2$, $R_3$ and m are defined as in formula I, subsequently substituting phenyl, if $R_3$ denotes phenyl, (h) modifying a radical $R_2$ or substituents optionally present in $R_1$ if $R_1$ is a substituted phenyl ring in a manner such that further compounds of the formula I are provided.

In method (a) the compounds II are oxidized in known manner, for example using manganese dioxide, potassium permanganate (cf. "Compendium of Organic Synthetic Methods", published by John Winley and Sons, Inc. (1971), pages 32-36). The carboxylic acids are converted into the amides by the conventional methods of the amide chlorides. The starting compounds of the formula II for method (a) may be prepared according to German patent application No. P 28 11 361.3, for example by reacting compounds of the formula VIII

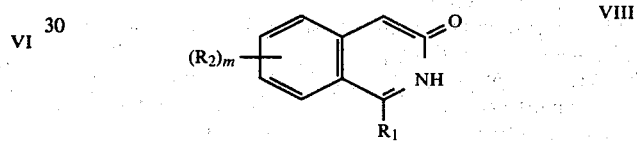

wherein $R_1$, $R_2$ and m are defined as in formula I with a Vilsmeier addition product of an acid amide with an acid chloride or bromide to yield a compound of the formula IX

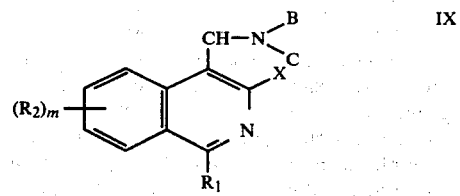

wherein X is chlorine or bromine and B and C each are alkyl or cycloalkyl having from one to six carbon atoms or phenyl and by subsequently oxidizing the compounds of the formula II.

In method (b) the compounds I and II are reduced in known manner. Suitable reduction agents are, for example complex metal hydrides such as sodium boron hydride, lithium aluminum hydride and suitable solvents are methanol, ethanol, tetrahydrofuran and dimethoxyethane.

In method (c) the compounds IV are reduced in known manner, using as reduction agent, by way of example, metal hydrides such as sodium boron hydride, lithium aluminum hydride and as solvents methanol, ethanol, tetrahydrofuran and dimethoxyethane. The compounds IV may be obtained from the compounds II by reaction with an amine with acid catalysis. In this process the reaction water formed may be separated preferably by means of a water separator.

In method (d) the compounds V are reacted with an amine in the presence of a hydrogen halide-binding agent. As hydrogen halide-binding agent an excess of amine may used or tertiary amines such as triethylamine, pyridine or potassium carbonate or the like. As suitable solvents, as far as they are used for the reaction, there may be mentioned indifferent, anhydrous organic solvents such as dioxan, dimethoxyethane, diethylene glycol dimethyl ether, diethylene glycol dibutyl ether, benzene, toluene, xylene, chlorobenzene, dimethylformamide, dimethylsulfoxide or hexamethylphosphoric acid triamide. The reaction is carried out generally at a temperature from 20° to 180° C., preferably from 20° to 130° C. The compounds required for method (g) may be prepared by reacting compounds V with halogenation agents such as phosphorus trichloride, phosphorus tribromide in known manner.

As agents splitting off water in method (e) there may be used, by way of example, phosphorus pentoxide, phosphorus oxychloride, acetic acid anhydride. The reaction is carried out generally at a temperature from 50° to 150° C. using as solvents, by way of example, pyridine, benzene, toluene, N,N-dimethylformamide and the like.

According to method (f) secondary amino groups are alkylated in known manner with alkylation agents $Y-R_{10}$.

In method (g) substituents may be introduced into the aromatic radical $R_4$ by way of electrophilic substitution, this substitution including in particular halogenation, sulfonation or nitration, nitration being of particular interest. Nitration consists in submitting compounds of the formula I to the usual nitration conditions using, for example sulfuric acid, nitric acid and cooling with ice.

According to method (h) the substituents $R_4$ subsequently introduced into the radical $R_1$ or present in the radical $R_1$ may be modified subsequently, for example in the case of a nitro group by reduction, in the case of an amino group by alkylation or by splitting off ether, in the case of methoxy, in order to obtain further compounds of the formula I. The possibilities will by illustrated by way of example hereinafter. For example, reduction of an aromatic nitro group yields an amino group, for example the corresponding 4-aminophenyl group when $R_1$ denotes the 4-nitrophenyl radical. A reduction of this type is carried out in usual manner, for example in the presence of Raney nickel in ethanol or with the use of iron powder in hydrochloric solution. A further possibility consists in acylating an amino group. For example, $R_1$ may be converted into the 4-acetylaminophenyl radical, when it denotes the 4-aminophenyl radical, under the common conditions, for example with the use of acetanhydride in pyridine at low temperatures, in the range from 0° to 10° C. Or an aromatic amino group may be diazotized followed by reaction with a nucleophilic group. For example, if a radical $R_1$ denotes the 4-aminophenyl group, it may be converted into the corresponding diazonium salt with the use of nitrous acid, usually prepared from sodium nitrite and sulfuric acid, at low temperatures of 0° to 5° C., said salt yielding the 4-chlorophenyl radical when treated with hydrochloric acid in the presence of copper chloride or the 4-hydroxyphenyl group, upon being concentrated. Finally an alkoxy group may be cleaved to yield the corresponding hydroxy compound.

For example, the ether cleavage of a 7-methoxy compound in which $R_2$ is $OCH_3$ with the use of hydrogen bromide, for example, in aqueous acetic acid at a temperature from 50° to 120° C. yields the corresponding 7-hydroxy compound. Another possibility of modifying the substituents consists in oxidizing a methyl group to yield a carboxyl group or in reducing an aldoxime group to yield an amino group.

The compounds of the invention have valuable therapeutical properties. In addition to other pharmacological properties they act on the central nervous system. They are able to prevent convulsions started by electric current or by pentamethylenetetrazol and to prolong the thiopental or hexabarbital anaestesia. Owing to these properties the compounds of the invention may be used as active substances of medicaments having an antidepressive action.

The dosage required to treat a human patient suffering from depressions depends on the nature and the extent of the depression. Generally, small dosages will be administered initially with gradual increase in dosage until the optimum dosage level is determined for the particular patient under treatment. It will generally be found that when the composition is administered orally, larger quantities of the active ingredient will be required to produce the same antidepressive effect as would be produced by the smaller quantity of the active compound which is administered parenterally. In general, dosages will be in the range from about 50 to 500 mg/kg per day if administered orally, whereas dosages of from 20 to 300 mg/kg per day are used for intravenous administration.

The novel compounds may be used either by themselves or in conjunction with physiologically acceptable auxiliary agents or carriers. For oral administration the active compounds are mixed with the substances common for this purpose and are brought by usual methods into suitable dosage unit forms, such as tablets, gelatin capsules, aqueous, alcoholic or oily suspensions or aqueous alcoholic or oily solutions. As inert carriers there may be used, for example, magnesium carbonate, lactose or corn starch. The composition may be prepared in the form of dry or moist granules. As oily carriers or solvents there may be mentioned in particular vegetable and animal oils, for example sunflower oil or cod-liver oil.

A special way of administration is to be seen in the intravenous application. For this purpose the active compounds or the physiologically acceptable salts thereof are dissolved with the substances common for this process. Physiologically acceptable salts of this kind are formed, for example, with the following acids: hydrochloric, hydrobromic or hydriodic acid, phosphoric acid, sulfuric acid, methylsulfuric acid, amidosulfonic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, aceturic acid, embonic acid, naphthalene-1,5-disulfonic acid, ascorbic acid, phenylacetic acid, p-amino-salicylic acid, hydroxyethane-sulfonic acid, benzene-sulfonic acid, or synthetic resins which contain acid groups, for example those having an ion exchange effect. As solvents of the corresponding physiologically acceptable salts of the active compounds for introavenous application there may be mentioned, for example: water, physiological salt solutions or alcohols, such as ethanol, propanediol or glycerol, furthermore sugar solutions, for example glucose or mannitol solutions, or a mixture of the various solvents specified above.

The compounds of the formula I may show a great variety of further reactions and are therefore valuable intermediates for medicaments.

The invention will be illustrated in the following examples.

EXAMPLE 1

3-Chloro-1-phenyl-isoquinoline-4-carboxylic acid 53.5 g 3-Chloro-1-phenyl-isoquinoline-4-aldehyde are suspended in 1.5 l of acetone and 500 ml of phosphate buffer of pH 7. At 40° C., 40 g of potassium permanganate are introduced portionwise within 2 hours and stirring is continued at this temperature for 2 hours. The excess potassium permanganate is destroyed with 10 g sodium hydrogenosulfite and the solution is concentrated to 500 ml and filtered. The filtrate is brought to pH 4 with concentrated hydrochloric acid followed by thorough extraction with acetic ester. Removal of the solvent in vacuo provides 41.1 g of 3-chloro-1-phenyl-isoquinoline-4 carboxylic acid having a melting point of 208° C.

The following carboxylic acids of Table 1 are obtained from the corresponding aldehydes according to Example 1.

TABLE 1:

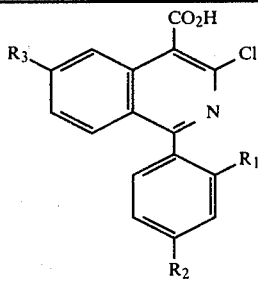

| Example | $R_1$ | $R_2$ | $R_3$ | $M_p$ |
|---|---|---|---|---|
| 2 | H | H | Cl | 268–271° C. |
| 3 | H | Cl | H | 230–237° C. |

TABLE 1:-continued

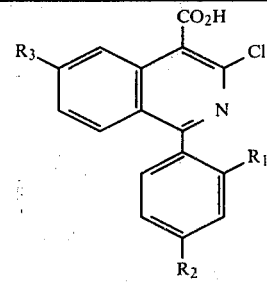

| Example | $R_1$ | $R_2$ | $R_3$ | $M_p$ |
|---|---|---|---|---|
| 4 | $CH_3$ | H | H | 105° C. |
| 5 | H | H | H | 180–184° C. |

EXAMPLE 6

3-Chloro-1-phenyl-isoquinoline-4-carboxylic acid N-methylpiperazide 11.3 g of 3-chloro-1-phenyl-isoquinoline-4-carboxylic acid chloride are added dropwise to 11.3 g N-methylpiperazine in 100 ml of chloroform at room temperature. The resulting mixture is left to stand at room temperature for 6 hours. Then the solvent is removed and the residue is stirred with saturated sodium hydrogenocarbonate solution. 13.3 g of the N-methylpiperazide having a melting point of from 164°–167° C. are isolated.

Hydrochloride 256° C.

Boiling of the corresponding carboxylic acid for 4 hours with the excess thionylchloride yields the 3-chloro-1-phenyl-isoquinoline-4-carboxylic acid chloride. The excess thionylchloride is removed leaving the crude acid chloride, which is further processed immediately.

Analogously to Example 6, the compounds of Table 2 are prepared from the corresponding acid chlorides and amines.

TABLE 2:

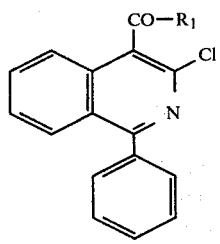

| Example | $R_1$ | $M_p$ | Salt | $(M_p)$ |
|---|---|---|---|---|
| 7 | —N(CH$_3$)$_2$ | 108° C. | | |
| 8 | —N⏜N—CH$_2$CH$_2$OH | 146–148° C. | HCl | (256–258° C.) |
| 9 | —NH—CH$_2$CH$_2$—N(C$_2$H$_5$)$_2$ | oil | oxalate | (167–169° C.) |
| 10 | —NH—CH$_2$CH$_2$CH$_2$—N(CH$_3$)$_2$ | 105–108° C. | HCl | (207–208° C.) |

TABLE 2:-continued

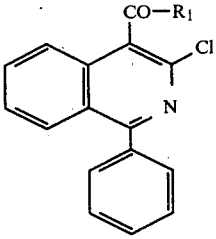

| Example | R₁ | $M_p$ | Salt | $(M_p)$ |
|---|---|---|---|---|
| 11 | -N\_/NH | 158-165° C. | HCl | (240-244° C.) |

EXAMPLE 12

3-Chloro-4-cyano-1-phenyl-isoquinoline 55.5 g Hydroxyamine hydrochloride is added to 53.6 g 3-chloro-1-phenyl-isoquinoline-4-aldehyde in 150 ml pyridine at 0° C. The resulting mixture is left to stand at room temperature for 2 hours. Then, successively, the solvent is removed in vacuo, the residue is partioned between water and toluene, the toluenic phase is dried and concentrated. 43.2 g 3-chloro-1-phenyl-isoquinoline-4-aldoxime having a melting point from 151° to 154° C. are obtained.

To convert aldoxime into the 4-cyano compounds, 91.4 g phosphoroxychloride are added to 67.3 g aldoxime in 700 ml of pyridine at 0° C. and the resulting mixture is left to stand at room temperature for 12 hours. The reaction mixture is hydrolyzed with water and the crystalline precipitate is filtered off. Dissolution of the precipitate in ethanol gives 47 g 3-chloro-4-cyano-1-phenyl-isoquinoline having a melting point from 191° to 193° C.

EXAMPLE 13

4-Aminomethyl-3-chloro-1-phenyl-isoquinoline 12.5 g 3-Chloro-1-phenyl-isoquinoline-4-aldoxime are hydrogenated in 500 ml of methanolic ammonia in the presence of 30 g of prehydrogenated Raney-nickel, at room temperature and under atmospheric pressure. After 30 minutes, the precipitate is filtered off from the catalyst, the solution is concentrated and the residue is chromatographed on 200 g of silica gel using a mixture of chloroform and methanol (8:2). 2.5 g 4-Aminomethyl-3-chloro-1-phenyl-isoquinoline having a melting point from 101° to 103° C. are isolated.

Hydrochloride 295° C.

EXAMPLE 14

3-Chloro-1-(4-chlorophenyl)-6,7-dimethoxy-4-(3-dimethylaminopropyl)-aminomethyl-isoquinoline 3.62 g 3-Chloro-1-(4-chlorophenyl)-6,7-dimethoxy-isoquinoline-4-aldehyde is heated to 80° C. within 4 hours in conjunction with 3.06 g of 3-dimethylaminopropylamine in 100 ml dimethylformamide (DMF) and 50 ml CH₃OH. The solvent is removed in vacuo, the residue is dissolved in 150 ml of anhydrous methanol and 1.53 g of sodium boron hydride are added portionwise at 10° C. The reaction mixture is stirred for 3 hours, the solvent is removed in vacuo and the residue is stirred with water. Filtration of the resulting mixture gives 4.2 g 3-chloro-1-(4-chlorophenyl)-6,7-dimethoxy-4-(3-dimethylaminopropyl)-aminomethyl-isoquinoline having a melting point from 126° to 127° C.

Dihydrochloride: 250° to 252° C.

EXAMPLE 15

3-Chloro-4-hydroxymethyl-1-phenyl-isoquinoline

To 8.1 g 3-Chloro-1-phenyl-isoquinoline-4-aldehyde in 150 ml methanol there are added portionwise 1.8 g sodium boron hydride at 0° C. The solution is stirred at room temperature for 4 hours and the solvent is removed in vacuo. The residue is stirred with water. Filtration of the resulting mixture gives 7.2 g 3-chloro-4-hydroxymethyl-1-phenyl-isoquinoline having a melting point from 175° to 182° C.

EXAMPLE 16

3-Chloro-4-dimethylaminomethyl-1-phenyl-isoquinoline 8.2 g 3-Chloro-4-hydroxymethyl-1-phenyl-isoquinoline are suspended in 300 ml toluene and 16.2 g phosphorus tribromide are added thereto while cooling with ice. After a 10 hours' stirring at room temperature dimethylamine is introduced until an alcaline reaction occurs. The reaction mixture is concentrated and water is added to the residue. Extraction with acetic acid ester gives a yellow oil, that crystallizes slowly. Melting point 75° to 77° C. Hydrochloride: 244° to 246° C.

EXAMPLE 17

3-Chloro-1-phenyl-isoquinoline-4-carboxylic acid N-methyl-piperazide 7.0 g 3-Chloro-1-phenyl-isoquinoline-4-carboxylic acid piperazide, 3.5 g methyl iodide and 3.6 g sodium carbonate are refluxed in 100 ml toluene for 3 hours. The inorganic precipitate is filtered off and the solvent is removed in vacuo leaving 6.2 g N-methyl-piperazide having a melting point from 164° to 167° C.

What is claimed is:

1. An isoquinoline of the formula

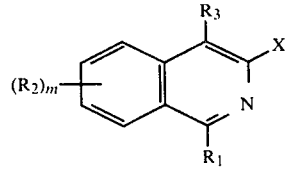

or a physiologically acceptable salt thereof in which m is 1 or 2:

X is chlorine or bromine;

R₁ is phenyl or phenyl mono- or disubstituted by halogen, hydroxy, alkyl or alkoxy each having one to six carbon atoms, trifluoromethyl, unsubstituted amino or amino substituted by one or two alkyl groups having from one to six carbon atoms;

R₂ is hydrogen, halogen, hydroxy, alkyl or alkoxy having from one to four carbon atoms or methylenedioxy;

R₃ is carboxyl, cyano, hydroxymethyl, aminoalkyl of the formula

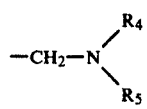

or a carboxylic acid amide of the formula

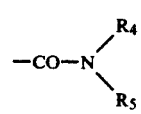

wherein R₄ and R₅ are identical or different and denote hydrogen or alkyl of 1 to 4 carbon atoms and wherein said alkyl may be substituted by an dialkylamino group

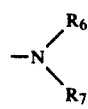

wherein R₆ and R₇ are identical or different and denote alkyl of from one to six carbon atoms; or R₄ and R₅ together with the nitrogen to which they are attached form a piperazine ring, the 4-nitrogen of which may be substituted by hydrogen, alkyl of one to four carbon atoms or hydroxy-alkyl of one to four carbon atoms.

2. An isoquinoline of the formula

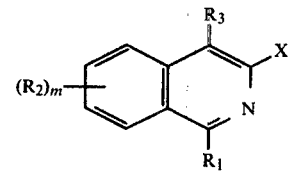

or a physiologically acceptable salt thereof in which m is 1 or 2; X is bromine or chlorine, R₁ is phenyl or phenyl substituted by halogen or alkyl of 1 to 4 carbon atoms; R₂ is hydrogen or halogen; and R₃ is carboxyl, cyano, hydroxymethyl, aminoalkyl of the formula

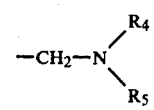

or a carboxylic acid amide of the formula

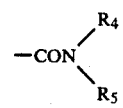

in which R₄ and R₅ are hydrogen or alkyl of 1 to 4 carbon atoms which may be substituted by dialkylamino of 2 to 4 carbon atoms, or R₄ and R₅ together with the nitrogen on which they are substituted form a piperazine ring, the 4-nitrogen atom of which may be substituted by alkyl of 1 to 4 carbon atoms or hydroxyalkyl of 1 to 4 carbon atoms.

3. Antidepressive composition comprising an effective amount of the compound as defined in claim 1 and a physiologically acceptable auxiliary agent or carrier therefor.

4. A method of treating a human patient having depressions which comprises orally administering to said patient an effective dosage of from about 50 to 500 mg/kg per day of a compound as defined in claim 1.

5. A method of treating a human patient having depressions which comprises intravenously administering to said patient an effective dosage of from about 20 to 300 mg/kg per day of a compound as defined in claim 1.

* * * * *